(12) United States Patent
Ongouta et al.

(10) Patent No.: US 11,197,491 B2
(45) Date of Patent: Dec. 14, 2021

(54) METHOD FOR PRODUCING UNSATURATED DECANALS

(71) Applicant: SYMRISE AG, Holzminden (DE)

(72) Inventors: Jekaterina Ongouta, Stadtoldendorf (DE); Michael Backes, Holzminden (DE); Jakob Peter Ley, Holzminden (DE); Volkmar Koppe, Höxter-Stahle (DE); Jens Koch, Eschershausen (DE)

(73) Assignee: SYMRISE AG, Holzminden (DE)

( * ) Notice: Subject to any disclaimer, the term of this patent is extended or adjusted under 35 U.S.C. 154(b) by 142 days.

(21) Appl. No.: 16/305,969

(22) PCT Filed: Jun. 2, 2016

(86) PCT No.: PCT/EP2016/062571
§ 371 (c)(1),
(2) Date: Nov. 30, 2018

(87) PCT Pub. No.: WO2017/207060
PCT Pub. Date: Dec. 7, 2017

(65) Prior Publication Data
US 2019/0289887 A1    Sep. 26, 2019

(51) Int. Cl.
| | |
|---|---|
| *A23L 27/20* | (2016.01) |
| *A23L 27/26* | (2016.01) |
| *C07C 45/65* | (2006.01) |
| *A23L 9/10* | (2016.01) |
| *C07C 45/54* | (2006.01) |
| *C07C 45/51* | (2006.01) |
| *A23L 19/18* | (2016.01) |
| *A23L 23/00* | (2016.01) |
| *C07C 45/53* | (2006.01) |
| *A23L 23/10* | (2016.01) |

(52) U.S. Cl.
CPC .............. *A23L 27/2024* (2016.08); *A23L 9/10* (2016.08); *A23L 19/18* (2016.08); *A23L 23/00* (2016.08); *A23L 23/10* (2016.08); *A23L 27/26* (2016.08); *C07C 45/517* (2013.01); *C07C 45/53* (2013.01); *C07C 45/54* (2013.01); *C07C 45/65* (2013.01); *A23V 2002/00* (2013.01)

(58) Field of Classification Search
CPC ...... A23L 27/2024; A23L 27/26; A23L 23/10; A23L 19/18; A23L 19/10; A23L 23/00; C07C 45/517; C07C 45/54; C07C 45/65; A23V 2002/00
USPC ................................................. 426/534, 650
See application file for complete search history.

(56) References Cited

U.S. PATENT DOCUMENTS 3,686,003 A    8/1972   Dorp et al.

OTHER PUBLICATIONS

International Search Report and Written Opinion dated Jan. 31, 2017 for corresponding PCT Application No. PCT/EP2016/062571.
Blank, I. et al., "Identification of Potent Odorants Formed by Autoxidation of Arachidonic Acid: Structure Elucidation and Synthesis of (E,Z,Z)-2,4,7,-Tridecatrienal", Journal of Agricultural and Food Chemistry, American Chemical Society, vol. 49, Nr. 6, 2001, pp. 2959-2965.

*Primary Examiner* — Leslie A Wong
(74) *Attorney, Agent, or Firm* — Polsinelli PC

(57) ABSTRACT

The present invention relates to a flavour mixture containing 2E,4Z,7Z- and 2E,4E,7Z-tridecatrienal. This flavour mixture can be produced advantageously from arachidonic acid or oils containing esters thereof.

11 Claims, No Drawings

METHOD FOR PRODUCING UNSATURATED DECANALS

CROSS-REFERENCE TO RELATED APPLICATIONS

This application is a national stage application (under 35 U.S.C. § 371) of PCT/EP2016/062571, filed Jun. 2, 2016, which is incorporated herein by reference in its entirety.

The present invention relates to flavour compositions and methods for the production thereof.

The targeted production and use of flavour mixtures of certain flavours, which are compatible with food law, is subject to continuous research efforts.

Unsaturated decanals are thereby among the interesting flavours, in particular 2E,4Z,7Z- and 2E,4E,7Z-tridecatrienal as well as 2E,4E-decadienal. These are characterized in many applications by a meat flavour, in particular chicken flavour.

The production of these flavours usually occurs fully synthetically from smaller components via coupling reactions, as e.g. in Blank et al., J. Agric. Food Chem. 2001, 2959.

Therefore, the problem of finding alternative and easier production methods for the production of unsaturated decanals arises.

This problem is solved by the method according to claim 1. According to this, a method for the production of unsaturated decanals, in particular 2E,4Z,7Z- and 2E,4E,7Z-tridecatrienal and/or 2E,4E-decadienal is presented comprising the steps
  a) Air oxidation of an educt containing Arachidonic acid or arachidonic acid ester
  b) Decomposition of the resulting peroxide
  c) Concentration It was found surprisingly, that thereby in many applications of the present invention, in particular 2E,4Z,7Z- and 2E,4E,7Z-tridecatrienal can be produced in a sensorially acceptable, in many cases even preferred quality.

In most of the applications of the present invention, one or several of the following advantages can be observed or received:
  The method is usable with confidence with respect to food technology and food law.
  The method can be repeated several times, in order to thereby increase the yield.
  The method does not require unconventional process steps or procedures, so that it is usable in conventional plants without problem.
  The method delivers a product with a complex flavour profile, which is described to be especially natural.
  The method relies on the use of renewable resources without the use of stoichiometric reagents.

The single steps of the method are explained in the following, wherein single steps are arbitrarily combinable with one another and single sub-steps or aspects are isolatedly preferred embodiments of the invention.

Step a) Air Oxidation

Under the term "Arachidonic acid or educt containing arachidonic acid ester", on the one hand pure Arachidonic acid ((5Z,8Z,11Z,14Z)-Icosa-5,8,11,14-tetraenoic acid) or esters thereof, preferably methyl-, ethyl- or hydroxyalkylesters, are to be understood, preferred hydroxyalkylesters are dihydroxypropyl arachidonic acid esters.

But this term is not limited thereon, also educts containing free Arachidonic acid or arachidonic acid esters can be used. Particularly preferred thereby is the use of an oil, which has Arachidonic acid as the substantial component of the contained glyceridically bound fatty acids. Preferred are thereby oils, which contain ≥20-≤80 wt.-% of bound Arachidonic acid, even preferred ≥35-≤45 wt.-% of Arachidonic acid.

According to a preferred embodiment of the present invention, the air oxidation occurs via gassing with air. The preferred air volume is ≥10-≤1000 l/h per kg of educt. This turned out to be advantageous. At lower air volumes, the yield is often too low, higher air volumes lead to the formation of side products or decomposition of the resulting desired products.

Especially preferred is an air volume of ≥30-≤500 l/h per kg, most preferred of ≥40-≤100 l/h per kg of educt.

Step a) is carried out preferably for a period of ≥1 to ≤20 h, preferably ≥2 h to ≤7 h. Longer reaction times have often turned out to be disadvantageous, as thereby undesired side products are formed in large amounts.

Step a) is carried out especially preferably at a temperature from ≥100° C. and ≤200° C.

Thereby, two temperature ranges in combination with different reaction periods are especially preferred:

According to a preferred embodiment, step a) is carried out at a temperature from ≥110° C. and ≤130° C. for ≥5-≤7 h.

Alternatively, according to a preferred embodiment, step a) is carried out at a temperature from ≥160° C. and ≤180° C. for ≥1-≤3 h.

Step a) can be carried out with pure educt. Alternatively, step a) is carried out in presence of a solvent. Preferred are Triacetin or Triethyl citrate. Especially preferred is Triacetin, preferably in an amount of ≥2-≤20 wt.-%, relative to the educt. Most preferred is the addition of ≥5-≤15 wt.-% of Triacetin.

According to a further preferred embodiment of the invention, before step a), at the use of an oil with a fraction of glyceridically bound Arachidonic acid or of another ester of Arachidonic acid, in addition to the Arachidonic acid bound in the oil, another free unsaturated fatty acid, preferably in an amount of ≥5-≤10 wt.-% relative to the educt, is added. Especially preferred are Linoleic acid, Linolenic acid and Arachidonic acid. Most preferred is Linolenic acid.

Step b)

Step b) occurs preferably by heating, preferably to temperatures of ≥100° C. and ≤200° C. Preferred reaction periods are ≥0.5-≤5 h.

Thereby, two temperature ranges in combination with different reaction periods are especially preferred:

According to a preferred embodiment, step b) is carried out at a temperature from ≥120° C. and ≤140° C. for ≥1.5-≤2.5 h.

Alternatively, according to a preferred embodiment, step b) is carried out at a temperature from ≥160° C. and ≤180° C. for ≥0.5-≤1.5 h.

Step c)

Step c) occurs preferably via fractional distillation. Thereby, optionally, according to a preferred embodiment, Triacetin still can be added before, preferably in an amount of ≥2-≤60 wt.-%, especially preferred ≥5-≤40 wt.-%, especially preferred ≥10-≤20 wt.-%, each relative to the parent compound.

Preferably, readily volatile compounds are thereby separated at first. This often turned out to be favourable, as in this way, in many applications, undesired green side notes, which arise from present hexanal or 2E-octenal, of the flavour mixture can be avoided in a simple manner.

According to a preferred embodiment, the method further comprises a step d).

d) Repeating, in particular repeating several times, the steps a) to c) in that order.

Preferably, the sequence from a) to c) is repeated in total three to five times, preferably four times.

The present invention furthermore relates to a flavour mixture, producible according to the method described above, as well as a food and/or a food supplement comprising flavour mixtures of this kind.

Preferably, the flavour mixture comprises one of the compounds 2E,4Z,7Z- and 2E,4E,7Z-tridecatrienal.

The present invention furthermore relates to formulated products/preparations comprising a flavour mixture, produced or producible according to the present method.

Thereby, these can be food and/or food supplements.

Thus, the present invention furthermore relates to a food and/or food supplement comprising the inventive flavour mixture.

Preferably, the ratio of the flavour mixture, relative to the food and/or food supplement, thereby is ≥0.0001 wt.-% (1 ppm) to ≤0.5 wt.-% (5000 ppm), preferably ≥0.0001 wt.-% (1 ppm) to ≤0.1 wt.-% (1000 ppm), especially preferably ≥0.001 wt.-% (10 ppm) to ≤0.05 wt.-% (500 ppm).

According to a preferred embodiment, the food and/or food supplements further contain volatile flavours.

Preferably, the food and/or food supplements contain one or more ingredients selected from the group containing volatile organic acids, alcohols, thiols and disulfides, heterocyclic compounds, in particular pyridines, pyrrolines, thiazoles and thiazolines, further aldehydes, ketones, esters/lactones or mixtures thereof.

Especially preferred ingredients—wherein arbitrary ingredients can be combined with one another in any manner—thereby are:

organic acids:
Acetic acid, Butanoic acid, 2- or 3-Methyl butanoic acid, respectively, Capric acid, Caproic acid, Phenyl acetic acid;

Alcohols:
Ethanol, Propylene glycol, 1,3-Octenol, cis-3-Hexenol, Linalool, Benzyl alcohol, p-Cresol, 2,6-Dimethylthiophenol, Guaiacol, Eugenol, Disulfides/thiols:
Dimethylsulfide, Difurfuryldisulfide, Methylthiopropanal, 2-Methyl-3-methyldithiofuran and Bis(2-methyl-3-furyl)disulfide, Methylfuranthiol, 2-(4-methyl-1,3-thiazol-5-yl)ethanol (Sulfurol), Methyltetrahydrofuranthiol, 3-Methyl-2-buten-1-thiol, 3-Thio-2-methylpentanol, 2-Furfurylthiol, Thiophenol, 2-Methylthiophenol and 2-Mercaptobutanon;

Pyridines:
2-Acetylpyridine; Pyrazine, further preferred Methylpyrazine, 2,5-Methylethylpyrazine, 2,3,5-Trimethylpyrazine, Acetyl pyrazine, 2,3-Diethyl-5-methylpyrazine, 2-Ethyl-3,5-dimethylpyrazine and 2-Isopropyl-3-methoxypyrazine;

Thiazoles/Thiazolines
2-Acetylthiazole, 2-Acetyl-2-thiazoline;

Pyrrolines:
2-Propionyl-1-pyrroline and 2-Acetyl-1-pyrroline;

further heterocyclic compounds:
Indole and Skatole.

Aldehydes:
Acetaldehyde, trans-4,5-Epoxy-(2E)-decenal, cis-4,5-Epoxy-(2E)-decenal, (E,E)-2,4-Undecadienal, (E,E)-2,4-Decadienal, (E,Z)-2,4-Decadienal, (E,E,Z)-2,4,6-Nonatrienal, (E,E)-2,4-Nonadienal, (E)-2-Undecenal, (Z)-2-Decenal, (E)-2-Decenal, (E)-2-Nonenal, (Z)-2-Nonenal, (E,Z)-2,6-Nonadienal, (E,E)-2,4-Nonadienal, 3-Methylthiopropanal (Methional), Vanillin and Phenylacetaldehyde;

Ketones:
3,4-Dimethylcyclopentan-1,2-dion, 3-Hydroxy-4,5-dimethylfuran-2(5H)-on (Sotolon), 2-Aminoacetophenon, 3-Hydroxy-4,5-dimethyl-2(5H)-furanon, 2,5-Dimethyl-4-hydroxy-3-[2H]-furanon (Furaneol©), Tetrahydrothiophen-3-on and 3-Thiobutan-2-on;

Esters and Lactones:
Methyl butanoate, Ethyl-3-methylbutanoate, Propyl-2-methylbutanoate, (Z)-≤6-Dodecen-γ-lactone, 4-Hydroxy-2-nonensäurelactone, δ-Undecalactone, γ-Nonalactone and γ-Octalactone.

The food and food supplements can comprise further flavours according to a preferred embodiment.

The flavour or the flavours can thereby be applied in the form of reaction flavours (Maillard-products), extracts or rather essential oils of plants or parts of plants or rather fractions thereof, smoke flavours or other flavouring preparations (e.g. [partial] protein hydrolysates, grill-like flavours, plant extracts, spices, preparations of spices, vegetable varieties, and/or preparations of vegetables).

Therefore, in particular flavours and their components, which are not comprised in the mixture and cause a roasty, meaty (in particular chicken, fish, seafood, beef, pork, lamb, sheep, goat), vegetably (in particular tomato, onion, garlic, celery, leek, mushrooms, aubergines, seaweed), a spicy (in particular black and white pepper, chili, paprika, cardamon, nutmeg, pimento, mustard and mustard products), roasted, yeasty, boiled, greasy, salty and/or spicy flavour impression and thus can strengthen the spicy impression.

As far as the present invention concerns preparations, these are preferably a preparation serving for nutrition and/or consumption, as well as semi-finished products for a preparation serving for nutrition and/or consumption or animal feed.

Preparations serving for nutrition or consumption in the sense of the invention are e.g. bakery products (e.g. bread, dry biscuits, cakes, other pastries), confectionery (e.g. chocolate bars, chocolate bar products, other bar products, fruit gums, hard and soft rolls, chewing gum), alcoholic or non-alcoholic beverages (e.g. Cocoa, coffee, green tea, black tea, (green, black) tea drinks enriched with (green, black) tea extracts, Roibos tea, other herbal teas, wine, wine-based drinks, beer, beer-based drinks, Liqueurs, spirits, brandies, fruit-based lemonades, isotonic drinks, soft drinks, nectars, fruit and vegetable juices, fruit or vegetable juice preparations), instant beverages (e.g. Instant cocoa drinks, instant tea drinks, instant coffee drinks), meat products (e.g. ham, fresh sausage or raw sausage preparations, seasoned or marinated fresh or salted meat products), eggs or egg products (dried egg, egg white, egg yolk), cereal products (e.g. breakfast cereals, muesli bars, pre-cooked ready-made rice products), dairy products (e.g. full-fat or fat-reduced or fat-free milk drinks, rice pudding, yoghurt, pudding, kefir, cream cheese, soft cheese, hard cheese, dried milk powder, whey, butter, buttermilk, partly or wholly hydrolysed products containing milk protein), products made from soy protein or other soybean fractions (e.g. soy milk and products made from it, beverages containing soy protein in isolation or enzymatically treated, beverages containing soy flour, preparations containing soy lecithin, fermented products such as tofu or tempe or products made from them and mixtures with fruit preparations and optional flavourings), Fruit preparations (e.g. jams, fruit ice cream, fruit sauces, fruit fillings), vegetable preparations (e.g. ketchup, sauces, dried vegetables, frozen vegetables, pre-cooked vegetables, cooked vegetables), snacks (e.g. baked or deep-fried potato crisps or potato dough products, extrudates based on maize or peanuts), fat- and oil-based products or emulsions thereof (e.g. mayonnaise, remoulade, dressings, in each case full-fat or fat-reduced), other instant meals and soups (e.g. dry soups, instant soups, pre-cooked soups), spices, seasoning mixes and in particular seasonings, which are used for example in the snack sector, sweetener preparations, tablets or sachets, other preparations for sweetening or whitening of drinks or other foodstuffs. The preparations in the sense of the invention may also serve as semi-finished goods for the manufacture of other preparations intended for human consumption or enjoyment.

As further ingredients for preparations in accordance with the invention, common raw materials, auxiliaries and additives for foodstuffs or luxury foods can be used. Some of these substances have an unpleasant taste in the sense of the above-mentioned definition.

Further customary active ingredients, basic substances, auxiliaries and additives for nutrition or enjoyment can be contained in amounts of 5 to 99.999999% by weight, preferably 10 to 80% by weight, based on the total weight of the preparation. Furthermore, the preparations may contain water in an amount up to 99.999999% by weight, preferably 5 to 80% by weight, based on the total weight of the preparation. Examples of common basic, auxiliary and additive substances for inventive preparations are water, mixtures of fresh or processed, vegetable or animal basic or raw materials (e.g. raw, roasted, dried, fermented, smoked and/or cooked meat, bones, cartilage, fish, vegetables, fruits, herbs, nuts, vegetable or fruit juices or pastes or mixtures thereof), digestible or nondigestible carbohydrates (e.g. sucrose, maltose, fructose, glucose, dextrins, amylose, amylopectin, inulin, xylans, cellulose), sugar alcohols (e.g. sorbitol), natural or hydrogenated fats (e.g. tallow, lard, palm fat, coconut fat, hydrogenated vegetable fat), oils (e.g. sunflower oil, peanut oil, corn oil, olive oil, fish oil, soya oil, sesame oil), fatty acids or their salts (e.g. potassium stearate), proteinogenic or non-proteinogenic amino acids and related compounds (e.g. taurine), peptides, native or processed proteins (e.g. gelatine), enzymes (e.g. peptidases), nucleic acids, nucleotides, taste correctives other than those used according to the invention for unpleasant taste impressions (e.g. Hesperetin, Phloretin or other hydroxychalcone derivatives to be used in accordance with US 2008/0227867 and, if applicable, the lactones described therein), taste corrigents for further, generally not unpleasant taste impressions, taste modulating substances (e.g. Inositol phosphate, nucleotides such as Guanosine monophosphate, Adenosine monophosphate or other substances such as Sodium glutamate or 2-Phenoxypropionic acid), emulsifiers (e.g. lecithins, diacylglycerols), stabilizers (e.g. Carrageenan, Alginate), preservatives (e.g. Benzoic acid, Sorbic acid), antioxidants (e.g. Tocopherol, Ascorbic acid), chelators (e.g. Citric acid), organic or inorganic acidifiers (e.g. Malic acid, Acetic acid, Citric acid, Tartaric acid, Phosphoric acid, Lactic acid), additional bitter substances (e.g. Quinine, Caffeine, Limonine, Amarogentin, humolones, lupolones, catechins, tannins), sweeteners (e.g. Saccharin, Cyclamate, Aspartame, Neotame, steviosides, rebaudiosides, Acesulfame K, Neohesperidine dihydrochalcone, Thaumatin, Superaspartam), mineral salts (e.g. Sodium chloride, Potassium chloride, Magnesium chloride, Sodium phosphates), enzymatic browning inhibitors (e.g. sulphite, Ascorbic acid), essential oils, plant extracts, natural or synthetic dyes or colour pigments (e.g. carotenoids, flavonoids, anthocyanins, chlorophyll and their derivatives), spices, synthetic, natural or nature-identical flavouring substances or perfumes as well as odor correctives.

The aforementioned components as well as the claimed components to be used in accordance with the invention described in the Application Examples are not subject to any special exceptional conditions in their size, shape, material selection and technical conception, so that the selection criteria known in the field of application can be applied without restriction.

Further details, features and advantages of the subject-matter of the invention result from the subclaims as well as from the following description of the associated examples, which are purely illustrative and not to be understood as restrictive:

EXAMPLE 1

100 g of oil containing Arachidonic acid (40% Arachidonic acid) is diluted with 10 g Triacetin and gassed at 120° C. with air (40 L/h) for 6 h. Subsequently, the reaction mixture is heated for 2 h at 130° C. The raw product is distilled in vacuum. Firstly, the readily volatile compounds are separated (Conditions: 0.1 mbar, 100° C., 30 min). The desired product is then distilled off with Triacetin. (Conditions: 0.1 mbar, 170° C., 1 h (F2)).

After destillative purification, the obtained solution (5.7 g) contains 50 mg of 2E,4Z,7Z- and 2E,4E,7Z-tridecatrienal in the ratio of 1:1.

EXAMPLE 2

The process according to Example 1 is repeated four times in total. 23.3 g of solution containing 120 mg of 2E,4Z,7Z- and 2E,4E,7Z-tridecatrienal in the ratio of 1:1 are obtained.

This solution is subsequently diluted with Triacetin, so that a mixture is generated, which contains in total 0.2 wt.-% of the corresponding 2E,4Z,7Z- and 2E,4E,7Z-tridecatrienals.

EXAMPLE 3

100 g of oil containing Arachidonic acid (40% Arachidonic acid) is gassed at 170° C. with air (40 L/h) for 2 h. Subsequently, the reaction mixture is heated for 1 h at 170° C. The raw product is diluted with 10 g Triacetin and distilled in vacuum. Firstly, the readily volatile compounds are separated (Conditions: 0.1 mbar, 100° C., 30 min). The desired product is then distilled off with Triacetin. (Conditions: 0.1 mbar, 170° C., 1 h (F2)).

After destillative purification, the obtained solution (7.7 g) contains 80 mg of 2E,4Z,7Z- and 2E,4E,7Z-tridecatrienal in the ratio of 1:4.

EXAMPLE 4

The process from Example 3 is repeated four times in total. 29.7 g of solution containing 230 mg of 2E,4Z,7Z- and 2E,4E,7Z-tridecatrienal in the ratio of 1:4 are obtained.

This solution is subsequently diluted with Triacetin, so that a mixture is generated, which contains in total 0.2 wt.-% of the corresponding 2E,4Z,7Z- and 2E,4E,7Z-tridecatrienals.

Application of the Flavour Mixture:

In the following, uses of a flavour mixture according to the inventive procedure are described. These are—to avoid confusion—referred to as "compositions".

EXAMPLE 1: PRODUCTION OF A CHICKEN FLAVOUR MIXTURE COMPRISING THE INVENTIVE FLAVOUR MIXTURE

Mixed are:

| Component | [G] |
|---|---|
| Acetylmethylcarbinol | 0.2 |
| Butanoic acid | 2 |
| Caproic acid | 1 |
| Caprylic acid | 1 |
| Decadienal trans, trans-2,4 | 0.8 |
| 2E-Decenal | 0.2 |
| Dimethyloxyfuranone/Sotolon 1% Solution in alcohol | 0.4 |
| Furaneol 10% Solution in Triacetin | 20 |
| Indole 1% Solution in alcohol | 0.4 |
| 2,3-Methylfuranthiol | 0.8 |
| Methyltetrahydrofuranthiol | 0.3 |
| Methylthiopropanal-3 | 0.15 |
| 3,2-Thiobutanon | 1 |
| Reaction product from Example 4 | 15 |
| Plant oil triglycerides | 956.75 |
| Sum | 1000 |

This flavour composition is used in the Application Examples described in the following.

EXAMPLE 2: PRODUCTION OF A CATTLE MARROWBONE FLAVOUR MIXTURE

Mixed are:

| Component | [G] |
|---|---|
| Acetylmethylcarbinol | 2 |
| Alcohol C6 | 0.5 |
| p-Cresol 1% Solution in PG | 5 |
| Decadienal trans, trans-2,4 5% in Triacetin | 50 |
| delta-Decalactone | 1.4 |
| delta-Dodecalactone | 3.5 |
| Furaneol 10% Solution in Triethyl citrate | 30 |
| Furfurylmercaptan 1% in Triethyl citrate | 3 |
| Indole 1% in alcohol | 5 |
| 2,3-Methylfuranthiol 5% A 1% in Triacetin | 60 |
| Methylthiopropanal-3 1% in Triethylcitrat | 15 |
| Myristinsäure | 4 |
| 2,3-Pentandion | 3 |
| 3,2-Thiobutanon 10% in plant oil triglycerides | 12 |
| 2,3,5-Trimethylpyrazin | 1 |
| Reaction product from Example 2 | 4 |
| plant oil triglycerides | 800.6 |
| Sum | 1000 |

This flavour composition is used in the Application Examples described in the following.

APPLICATION EXAMPLE 3: EGG PUDDING FLAVOUR COMPOSITION

Mixed are:

| Component | [G] |
|---|---|
| Acetylpyrazine-2 | 3 |
| Butanoic acid | 1 |
| Capric acid | 200 |
| Decadienal trans, trans-2,4 0.01% in Propylene glycol | 0.05 |
| delta-Decalactone | 50 |
| Diacetyl | 0.1 |
| delta-Dodecalactone | 100 |
| Furaneol 15% Solution in Propylene glycol | 0.1 |
| Indole FF 1% Propylene glycol | 0.75 |
| 2,3-Methylfuranthiol 0.005% in Triacetin | 40 |
| 1,2-Propylenglycol | 535 |
| Reaction product from Example 4 | 50 |
| Vanillin | 20 |
| Sum | |

This flavour composition is used in the Application Examples described in the following.

APPLICATION EXAMPLE 4: SPRAY DRIED FLAVOUR COMPOSITION

Based on the Application Examples 1 to 3 described above, four flavour compositions 4A to 4C are produced, which will be used further in the following:

| Ingredient | A | B | C |
|---|---|---|---|
| Capsul | 200 g | 200 g | 200 g |
| Maltodextrin | 600 g | 600 g | 600 g |
| Flavour composition Composition Application Example 1 | 200 g | — | — |
| Flavour composition Composition Application Example 2 | — | 200 g | — |
| Flavour composition Composition Application Example 3 | — | — | 200 g |
| Water | 1000 g | 1000 g | 1000 g |

The components are dissolved in demineralized water and subsequently spray dried. These are used in the following Application Examples.

APPLICATION EXAMPLE 5: INSTANT SOUP, TYPE CHICKEN SOUP WITH NOODLES

A=comparative preparation
B=preparations according to the invention

| Ingredient | A | B |
|---|---|---|
| Starch | 16 g | 16 g |
| Cooking salt | 7 g | 7 g |
| Sucrose, refined | 3.2 g | 3.2 g |
| Sodium glutamate | 3.2 g | 3.2 g |
| Sodium inosinate/Sodium guanylate in the ratio 1:1 | 0.8 g | 0.8 g |
| Plant protein hydrolysed by acid | 8.0 g | 8.0 g |
| Fat powder | 2.0 g | 2.0 g |
| Vegetable fat, spray dried | 1.0 g | 1.0 g |
| Freeze dried chicken meat, in pieces | 2.15 g | 2.15 g |
| Soup noodles | 32.0 g | 32.0 g |
| Maltodextrin | 12.0 g | 7.6 g |
| Chinese vegetable, freeze dried | 4.6 g | 4.6 g |
| Chicken flavour | 8.0 g | 6.9 g |

-continued

| Ingredient | A | B |
| --- | --- | --- |
| Food colouring Riboflavin | 0.05 g | 0.05 g |
| Spray dried flavour compositions from Application Example 4A | — | 5.5 g |

4.6 g of the respective powder mixture are boiled for 10 minutes in 100 ml water each to obtain a ready-to-eat soup. The inventive preparation B is rated stronger and longer lasting in terms of desired greasy aromas, reminiscent of chicken skin, resulting in a distinctly more authentic profile.

APPLICATION EXAMPLE 6: INSTANT SOUP, TYPE BEEF SOUP WITH NOODLES

A=comparative preparation
B=preparations according to the invention

| Ingredient | A | B |
| --- | --- | --- |
| Starch | 16 g | 16 g |
| Cooking salt | 7 g | 7 g |
| Sucrose, refined | 3.2 g | 3.2 g |
| Sodium glutamate | 3.2 g | 3.2 g |
| Sodium inosinate/Sodium guanylate in the ratio 1:1 | 0.8 g | 0.8 g |
| Plant protein hydrolysed by acid | 8.0 g | 8.0 g |
| Fat powder | 2.0 g | 2.0 g |
| Vegetable fat, spray dried | 1.0 g | 1.0 g |
| Freeze dried beef, in pieces | 2.15 g | 2.15 g |
| Soup noodles | 32.0 g | 32.0 g |
| Maltodextrin | 12.0 g | 11.1 g |
| Vegetable, freeze dried | 4.6 g | 4.6 g |
| Meat flavour | 8.0 g | 7.8 g |
| Food colouring Riboflavin | 0.05 g | 0.05 g |
| Spray dried flavour compositions from Application Example 4B | — | 1.1 g |

4.6 g of the respective powder mixture is boiled for 10 minutes in 100 ml of water each to obtain a ready-to-eat soup. By the use of the inventive flavour composition with Tridecatrienal, a greasy, full-bodied taste with an authentic profile is achieved, which was preferred to preparation A in the tasting by a panel of trained test persons.

APPLICATION EXAMPLE 7: BOUILLON

A=comparative preparation
B, C=preparations according to the invention

| Ingredient | A | B | C |
| --- | --- | --- | --- |
| Fat powder | 8.77 g | 8.77 g | 8.77 g |
| Sodium glutamate | 8.77 g | 8.77 g | 8.77 g |
| Yeast extract powder | 12.28 g | 12.28 g | 12.28 g |
| Cooking salt | 29.83 g | 29.83 g | 29.83 g |
| Maltodextrin | 37.28 g | 20.78 g | 33.78 g |
| Natural vegetable extract | 3.07 g | 3.07 g | 3.07 g |
| Spray dried flavour composition Application Example 4A | — | 16.5 g | — |
| Spray dried flavour composition Application Example 4B | — | — | 3.5 g |

15 g of the respective powder mixture is infused with 1000 ml of hot water. During the tasting by a panel of trained test persons, the inventive preparations B and C are evaluated as significantly richer, more balanced, stronger and more long-lasting than the comparative preparation A with respect to their flavour and taste.

APPLICATION EXAMPLE 8: VANILLA COOKED PUDDING

A=comparative preparation
B=preparations according to the invention

| Ingredient | A | B |
| --- | --- | --- |
| Sucrose | 7.8 g | 7.8 g |
| Starch | 3.0 g | 3.0 g |
| Skimmed milk powder | 1.5 g | 1.5 g |
| Aubygel MR50 | 0.5 g | 0.5 g |
| Extract of vanilla beans, spray dried, Symrise | 0.1 g | 0.1 g |
| Spray dried flavour compositions Application Example 4C | — | 0.25 g |
| Milk 1.5% fat content | ad 100 g | |

The solids are provided and stirred with the milk. The mixture is warmed to 95° C. for 2 minutes while stirring well, bottled and cooled to 5-8° C. The milk is then added to the mixture. By the use of the inventive flavour composition with Tridecatrienal, a clearly greasy, authentic taste with a pronounced egg note is achieved.

APPLICATION EXAMPLE 9: WHITE SAUCE

A=comparative preparation
B, C=preparation according to the invention

| Component | A | B | C |
| --- | --- | --- | --- |
| Maltodextrin | 26.00 g | 23.25 g | 25.40 g |
| Cooking salt | 7.50 g | 7.50 g | 7.50 g |
| Sodium glutamate | 2.00 g | 2.00 g | 2.00 g |
| Plant fat | 5.00 g | 5.00 g | 5.00 g |
| Pepper, white | 0.02 g | 0.02 g | 0.02 g |
| Onion powder | 1.48 g | 1.48 g | 1.48 g |
| pregelatinised maize starch | 30.00 g | 30.00 g | 30.00 g |
| Fat powder | 28.00 g | 28.00 g | 28.00 g |
| Spray dried composition Application Example 4A | — | 2.75 g | — |
| Spray dried composition Application Example 4B | — | — | 0.6 g |

90 g of the sauce mixture is infused with 1000 ml of hot water and stirred vigorously with the wire whisk. During the tasting by a panel of trained test persons, the inventive preparations B and C are evaluated as significantly richer, more balanced, stronger and longer-lasting than the comparative preparation A with regard to their flavour and taste.

APPLICATION EXAMPLE 10: BROWN SAUCE

A=comparative preparation
B=preparation according to the invention

| Component | A | B | C |
| --- | --- | --- | --- |
| Starch | 40.00 g | 40.00 g | 40.00 g |
| Maltodextrin | 33.10 g | 30.35 g | 32.50 g |
| Cooking salt | 6.00 g | 6.00 g | 6.00 g |
| Caramels, spray dried | 5.00 g | 5.00 g | 5.00 g |
| Yeast extract powder | 3.00 g | 3.00 g | 3.00 g |
| Sodium glutamate | 2.00 g | 2.00 g | 2.00 g |
| Sugar | 0.50 g | 0.50 g | 0.50 g |
| Fat powder | 5.00 g | 5.00 g | 5.00 g |
| Tomato powder | 3.00 g | 3.00 g | 3.00 g |
| Natural vegetable extract | 1.00 g | 1.00 g | 1.00 g |
| Onion extract | 0.30 g | 0.30 g | 0.30 g |

-continued

| Component | A | B | C |
|---|---|---|---|
| Pepper extract | 0.10 g | 0.10 g | 0.10 g |
| Dry flavour | 1.00 g | 1.00 g | 1.00 g |
| Spray dried composition Application Example 4A | — | 2.75 g | — |
| Spray dried composition Application Example 4B | — | — | 0.6 g |

90 g of the sauce mixture is infused with 1000 ml of hot water and stirred vigorously with the wire whisk. During the tasting by a panel of trained test persons, the inventive preparations B and C are evaluated as significantly richer, more balanced, stronger and longer-lasting than the comparative preparation A with regard to their flavour and taste.

APPLICATION EXAMPLE 11: SEASONING MIXTURE FOR POTATO CHIPS

A=comparative preparation
B=preparations according to the invention

| Component | A | B |
|---|---|---|
| Sodium glutamate | 3.50 g | 3.50 g |
| Cheese powder | 10.00 g | 10.00 g |
| Garlic powder | 2.00 g | 2.00 g |
| Whey powder | 38.86 g | 36.86 g |
| Spice extract oil | 0.20 g | 0.20 g |
| Paprika powder | 9.80 g | 9.80 g |
| Cooking salt | 21.00 g | 19.00 g |
| Tomato powder | 9.00 g | 9.00 g |
| Dry flavour | 2.50 g | 2.50 g |
| Silicon dioxide | 0.02 g | 0.02 g |
| Plant oil | 0.02 g | 0.02 g |
| Onion powder | 3.00 g | 3.00 g |
| Cream flavour concentrate | 0.03 g | 0.03 g |
| Cheese flavour | 0.03 g | 0.03 g |
| Tomato flavour concentrate | 0.04 g | 0.04 g |
| Spray dried composition Application Example 4A | — | 4.00 g |

6 g of the seasoning mixture are spread on 94 g of potato chips.

APPLICATION EXAMPLE 12: BEEF SEASONING MIXTURE FOR (INSTANT) NOODLES

| Ingredient | Gew.-% |
|---|---|
| Cattle fat flavour | 5.00 |
| Caramel | 3.00 |
| Citric acid (water free) | 0.40 |
| Wild chive (drained) | 2.00 |
| Maltodextrin (ex Tapoica) | 10.30 |
| Monosodium glutamate | 15.00 |
| Onion powder | 5.00 |
| Ribotide | 0.80 |
| Sodium chloride | 44.20 |
| Sugar | 2.80 |
| Sweet whey powder | 6.50 |
| Spray dried composition Application Example 4B | 5.00 |

All ingredients are mixed, until a homogeneous mixture is obtained.

APPLICATION EXAMPLE 13: CHICKEN MEAT SEASONING MIXTURE FOR (INSTANT) NOODLES

| Ingredient | Gew.-% |
|---|---|
| Chicken flavour | 5.00 |
| Caramel | 3.00 |
| Citric acid (water free) | 0.40 |
| Wild chive (drained) | 2.00 |
| Maltodextrin (ex Tapoica) | 5.30 |
| Monosodium glutamate | 15.00 |
| Onion powder | 5.00 |
| Ribotide | 0.80 |
| Sodium chloride | 39.20 |
| Sugar | 2.80 |
| Sweet whey powder | 6.50 |
| Spray dried composition Application Example 4A | 15.00 |

All ingredients are mixed, until a homogeneous mixture is obtained.

The individual combinations of the components and features of the above-mentioned statements are exemplary; the exchange and substitution of these teachings with other teachings contained in this publication with the cited publications are also expressly considered. The person skilled in the art recognizes that variations, modifications and other embodiments described here may also occur without deviating from the inventive idea and the scope of the invention. Accordingly, the above description is to be regarded as exemplary and not restrictive. The word "comprise" used in the claims does not exclude other elements or steps. The indefinite article "a" does not exclude the meaning of a plural. The mere fact that certain measures are recited in mutually different claims does not make it clear that a combination of these measures cannot be used to advantage. The scope of the invention is defined in the following claims and the corresponding equivalents.

The invention claimed is:

1. A method for producing unsaturated decanals comprising:
   a) air oxidizing an educt comprising arachidonic acid or arachidonic acid ester,
      wherein the educt is with a solvent selected from triacetin, triethyl citrate, and a combination thereof, and the solvent is in an amount of $\geq 2\text{-}\leq 20$ wt, %, relative to the educt,
   b) decomposing a resulting peroxide by heating at a temperature of $\geq 100°$ C. to $\leq 200°$ C. for $\geq 0.5$ h-$\leq 5$ h, and forming unsaturated decanals, and
   c) concentrating the unsaturated decanals.

2. The method according to claim 1 further comprising:
   d) repeating a) to c) in that order.

3. The method according to claim 1, wherein a) comprises gassing with air at an air volume $\geq 10\text{-}\leq 1000$ l/h per kg.

4. The method according to claim 1, wherein a) is carried out at a temperature of $\geq 100°$ C. and $\leq 200°$ C.

5. The method according to claim 1, wherein a) is carried out for a period of $\geq 1$ h to $\leq 20$ h.

6. The method according to claim 1, wherein c) comprises a fractional distillation.

7. The method according to claim 2, wherein a) comprises gassing with air at an air volume $\geq 10\text{-}\leq 1000$ l/h per kg.

8. The method according to claim 7, wherein a) is carried out at a temperature of $\geq 100°$ C. and $\leq 200°$ C.

9. The method according to claim 8, wherein a) is carried out for a period of $\geq 1$ h to $\leq 20$ h.

10. The method according to claim 1, wherein the unsaturated decanals are chosen from 2E,4Z,7Z-tridecatrienal, 2E,4E,7Z-tridecatrienal, and 2E,4E-decadienal.

11. The method according to claim 10 further comprising:
d) repeating a) to c) in that order.

* * * * *